United States Patent [19]
Stevens et al.

[11] Patent Number: 6,100,287
[45] Date of Patent: Aug. 8, 2000

[54] MATERIALS AND METHODS FOR ENHANCING MUSCLE PERFORMANCE AND RECOVERY FROM FATIGUE

[75] Inventors: Bruce R. Stevens, Gainesville; Michael D. Godfrey, Jacksonville; Thomas William Kaminski; Randy Wayne Braith, both of Gainesville, all of Fla.

[73] Assignee: University of Florida, Gainesville, Fla.

[21] Appl. No.: 09/192,119

[22] Filed: Nov. 13, 1998

Related U.S. Application Data

[60] Provisional application No. 60/065,429, Nov. 13, 1997.

[51] Int. Cl.$^7$ ........................ A61K 31/415; A61K 31/195
[52] U.S. Cl. ............................ 514/400; 514/561; 514/565
[58] Field of Search .................................... 514/400, 561, 514/565

[56] References Cited

U.S. PATENT DOCUMENTS 4,677,121 6/1987 Walser et al. .

FOREIGN PATENT DOCUMENTS

| 59-210871 | 11/1984 | Japan . |
| 03128318 | 5/1991 | Japan . |
| 08198748 | 8/1996 | Japan . |
| 09052828 | 2/1997 | Japan . |
| 8903688 | 5/1989 | WIPO . |
| 9512991 | 5/1995 | WIPO . |

OTHER PUBLICATIONS

MacDougall, J.D., M.A. Tarnopolsky, A. Chesley, S.A. Atkinson (1992) "Changes in muscle protein synthesis following heavy resistance exercise in humans: a pilot study" *Acta Physiol. Scand.* 146:403–404.

Snow, Christopher J., Katherine Blacklin (1992) "Reliability of Knee Flexor Peak Torque Measurements From A Standardized Test Protocol on a Kin/Com Dynamometer" *Arch Phys Med Rehabil.* 73:15–21.

Baker, A.J., K.G. Kostov, R.G. Miller, M.W. Weiner (1993) "Slow force recovery after long–duration exercise: metabolic and activation factors in muscle fatigue" *Journal of Applied Physiol.* 74:2294–2300.

Cerra, Frank B. (1992) "Role of Nutrition in the Management of Malnutrition and Immune Dysfunction of Trauma" *J. American College of Nutrition* 11(5):512–518.

Walser, Mackenzie, Norman D. LaFrance, Lynne Ward, Mary Ann VanDuyn (1987) "Progression of chronic renal failure in patients given ketoacids following amino acids" *Kidney International* 32:123–128.

Pui, Yurk Mui Lee and Hans Fisher (1979) "Factorial Supplementation with Arginine and Glycine on Nitrogen Retention/and Body Weight Gain in the Traumatized Rat" *J. Nutr.* 109:240–246.

Mitch, William E., Mackenzie Walser, Daniel G. Sapir (1981) "Nitrogen Sparing Induced by Leucine Compared with That Induced by its Keto Analogue, α–Ketoisocaproate, in Fasting Obese Man" *J. Clin. Invest.* 67:553–562.

Aftring, R. Paul, Kevin P. Block, Maria G. Buse (1986) "Leucine and isoleucine activate skeletal muscle branched–chain α–keto acid dehydrogenase in vivo" *Am. J. Physiol.* 250:E599–E604.

Buse, Maria G. and Sandra Reid (1975) "Leucine: A Possible Regulator Of Protein Turnover In Muscle" *J. Clin. Invest.* 56:1250–1261.

Abumrad, Naji N., K.L. Wise, P.E. Williams, N.A. Abumrad, W.W. Lacy (1982) "Disposal of α–ketoisocaproate: roles of liver, gut, and kidneys" *Am. J. Physiol.* 243:E123–E131.

Dudrick, Paul S. and Wiley W. Souba (1991) "Amino Acids in Surgical Nutrition: Principles and Practice" *Surg. Clin. N. Am.* 71(3):459–476.

Flakoll, P.J., M.J. VandeHaar, G. Kuhlman, S. Nissen (1991) "Influence of α–Ketoisocaproate on Lamb Growth, Feed Coversion, and Carcass Composition" *J. Anim. Sci.* 69:1461–1467.

Funk, Martha A., Karen R. Lowry, David H. Baker (1987) "Utilization of the L–and DL–Isomers of αKeto–β–methylvaleric Acids by Rats and Comparative Efficacy of the Keto Analogs of Branched–Chain Amino Acids Provided as Ornithine, Lysine and Histidine Salts" *J. Nutr.* 117:1550–1555.

Grunewald, Katharine K. and Robert S. Bailey (1993) "Commercially Marketed Supplements for Bodybuilding Athletes" *Sports Med.* 15:90–103.

Jeevanandam, Malayappa, Mohammad R. Ali, Nancy J. Holaday, Jeffery K. Weis, Scott R. Petersen (1993) "Relative nutritional efficacy of arginine and ornithine salts of α–ketoisocaproic acid in traumatized rats" *Am. J. Clin. Nutr.* 57:889–896.

Kasperek, George J. (1989) "Regulation of branched–chain 2–oxo acid dehydrogenase activity during exerccise" *Am. J. Physiol.* 256:E186–E190.

Kilberg, Michael S., Bruce R. Stevens, Donald A. Novak (1993) "Recent Advances in Mammalian Amino Acid Transport" *Annu. Rev. Nutr.* 13:137–165.

Lewis, Steven F. and Charles S. Fulco (1988) "A New Approach to Studying Muscle and Fatigue and Factors Affecting Performance During Dynamic Exercise in Humans" *Exercise Sports Med. Rev.* 26:91–116.

MacLean, D.A. and T.E. Graham (1993) "Branched–chain amino acid supplementation augments plasma ammonia responses during exercise in humans" *J. Appl. Physiol.* 74:2711–2717.

(List continued on next page.)

*Primary Examiner*—Raymond Henley, III
*Attorney, Agent, or Firm*—Saliwanchik, Lloyd & Saliwanchik

[57] ABSTRACT

The subject invention pertains to compositions and methods for enhancing muscle performance and recovery from fatigue in humans and animals. In a specific embodiment, the unique formulation is a glycine and L-arginine monohydrochloride salt of alphaketoisocaproic acid calcium (GAKIC).

19 Claims, 8 Drawing Sheets

OTHER PUBLICATIONS

MacLean, D.A., T.E. Graham, B. Saltin (1994) "Branched-chain amino acids augment ammonia metabolism while attenuating protein breakdown during exercise" *J. Appl. Physiol.* 267:E1010–E1022.

Mori, Eigo, Masaharu Hasebe, Kunio Kobayashi, Hiromasa Suzuki (1989) "Immediate Stimulation of Protein Metabolism in Burned Rats by Total Parenteral Nutrition Enriched in Branched–Chain Amino Acids" *J. Panenter. Enteral. Nutr.* 13:484–489.

Nissen, S., R. Sharp, M. Ray, J.A. Rathmacher, D. Rice, J.C. Fuller, Jr., A.S. Connelly, N.Abumrad (1996) "Effect of leucine metabolite β–hydroxy–β–methylbutyrate on muscle metabolism during resistance–exercise training" *J. Appl. Physiol.* 81:2095–2104.

Pan, Ming, Bruce R. Stevens, Wiley W. Souba (1944) "Regulation of Intestinal Amino Acid Transport: A Surgical Perspective" *Contemp. Surg.* 44:213–220.

Pan, Ming, Marc Malandro, Bruce R. Stevens (1995) "Regulation of system $y_{30}$arginine transport capacity in differentiating human intestinal Caco-2 cells" *Am. J. Physiol.* 268:G578–G585.

Pan, Ming and Bruce R. Stevens (1995) "Differentiation–and Protein Kinase C–dependent Regulation of Alanine Transport via System B" *J. Biol.Chem.* 270(8):3582–3587.

Harper A.E., R.H. Miller, K.P. Block (1984) "Branched–Chain Amino Acid Metabolism" *Ann. Rev. Nutr.* 4:409–454.

Benevenga, N.J. and R.D. Steele (1984) "Adverse Effects Of Excessive Consumption of Amino Acids" *Ann. Rev. Nutr.* 4:157–181.

Bazzarre, Terry L., Scott D. Murdoch, Shih–min L. Wu, David G. Herr, Ian P. Snider (1992) "Plasma Amino Acid Responses of Trained Athletes to Two Successive Exhaustion Trials With and Without Interim Carbohydrate Feeding" *J. Am. Coll. Nutr.* 11(5):501–511.

Barbul, Adian (1986) "Arginine: Biochemistry, Physiology, and Therapeutic Implications" *JPEN* 10(2):227–238.

Warren, B.J., M.H. Stone, J.T. Kearney, S.J. Fleck, R.L. Johnson, G.D. Wilson, W.J. Kraemer (1992) "Performance Measures, Blood Lactate and Plasma Ammonia as Indicators of Overwork in Elite Junior Weightlifters" *Int. J. Sports Med.* 13:372–376.

Visek, Williard J. (1986) "Arginine Needs, Physiological State and Usual Diets. A Reevaluation" *J. Nutr.* 116:36–46.

Koevering, Micheal Van and Steven Nissen (1992) "Oxidation of leucine and α–ketoisocaproate to β–methylbutyrate in vivo" *Am. J. Physiol.* 262(1 pt 1):E27–E31.

Tarnopolsky, Mark A., Stephanie A. Atkinson, J. Duncan Macdougael, Brett B. Senor, Peter W. R. Lemon, Henry Schwarcz (1991) "Whole body leucine metabolism during and after resistance exercise in fed humans" *Med. Sci. Sports Exerc.* 23:324–333.

Sapir, D.G., M. Walser, E.D. Moyer et al., (1983) "Effects of α–Ketoisocaproate And Of Leucne On Nitrogen Metabolism In Postoperative Patients" *Lancet* 1(8332):1010–1014.

Sitren, H.S. and H. Fisher (1977) "Nitrogen retention in rats fed on diets enriched with arginine and glycine" *r. J. Nutr.* 37:195–208.

Sandstedt, S., L. Jorfeldt, J. Larsson (1992) "Randomized, controlled study evaluating effects of branched chain amino acids and alpha–ketoisocaproate on protein metabolism after surgery" *Br. J. Surg.* 79:217–220.

Dohm, G. Lynis, George J. Kasperek, Edward B. Tapscott, Hisham A. Barakat (1985) "Protein metabolism during endurance exercise" *Fed. Proc.* 44:348–352.

Cynober, Luc, Michel Vaubourdolle, Alban Dore, Jacqueline Giboudeau (1984) "Kinetics and metabolic effects of orally administered ornithine α–ketoglutarate in healthy subjects fed with a standardized regimen" *Am. J. Clin. Nutr.* 39:514–519.

Cersosimo, Eugenio, Bonnie M. Miller, William W. Lacy, Naji N. Abumra (1983) "Alpha–Ketoisocaproate, Not Leucine, Is Responsible For Nitrogen Sparing During Progressive Fasting In Normal Male Volunteers" *Surg. Forum* 43:96–98.

Buckspan, Randy, Benjamin Hoxworth Eugenio Cersosimo, John Devlin, Eduard Horton, Naji Abumrad (1986) "α–Ketoisocaproate is superior to leucine in sparing glucose utilization in humans" *Am. J. Physiol.* 251:E648–653.

Blomstrand, E. and E.A Newsholme (1992) "Effect of branched–chain amino acid supplementation on the exercise–induced change in aromatic amino acid concentration in humam muscle" *Acta Physiol Scand* 146:293–298.

Cynober, Luc. Colette Coudray–Lucas, Jean–Pascal de Brandt et al. (1990) "Action of Ornithine α–Ketoglutarate, Ornithine Hydrochloride, and Calcium α–Ketoglutarate on Plasma Amino Acid and Hormonal Patterns in Healthy Subjects" *J. Am. Coll. Nutr.* 9(1):2–12.

TESTING PROTOCOL OVERVIEW

| VISIT | TREATMENT at t = -45, -20, 0 min | then EXHAUSTIVE EXERCISE SETS at t = 0, 5, 15 min |
|---|---|---|
| 1 (Day 0) | None | Maximal Force |
| 2 (Day 7) | GAKIC or Placebo | 0 min. set, 5 min. set, 15 min. set |
| 3 (Day 8) | None | 24 hour set |
| 4 (Day 22) | Default | 0 min. set, 5 min. set, 15 min. set |
| 5 (Day 23) | None | 24 hour set |

Double-Blind Repeated Measures Cross-Over Design

FIG. 2

MATERIALS AND METHODS FOR ENHANCING MUSCLE PERFORMANCE AND RECOVERY FROM FATIGUE

CROSS-REFERENCE TO A RELATED APPLICATION

This application claims priority from provisional application U.S. Ser. No. 60/065,429, filed Nov. 13, 1997.

BACKGROUND OF THE INVENTION

In the arena of athlete muscle performance, it is desirable to create conditions that permit competition or training at higher levels of resistance for a prolonged period of time. However, acute, intense anaerobic use of skeletal muscle often results in impaired athletic performance, with attendant losses in force and work output, and increased onset of muscle fatigue, soreness, and dysfunction. A single exhaustive exercise session—indeed, any acute trauma to the body such as muscle injury, resistance or exhaustive muscle exercise, or elective surgery—is characterized by perturbed metabolism that affects muscle performance in both acute and long term phases.

Exhaustive exercise depletes metabolic energy carbon sources and acutely disrupts skeletal muscle nitrogen metabolism in three principle ways. (1) Certain amino acids, including branched-chain amino acids, are released from muscle and are deaminated to elevate serum ammonia, oxidized locally as muscle fuel sources, and augment metabolic acidosis. (2) There is a decline in catalytic efficiency of muscle contraction events, as well as an alteration of enzymatic activities of nitrogen and energy metabolism. (3) Protein catabolism is initiated (including decreasing the rate of protein synthesis, as well as increasing degradation of non-contractible protein), thereby reducing long-term strength gains.

Recovery from fatigue during acute and extended exercise is associated with reversal of metabolic and non-metabolic fatiguing factors. Known factors that participate in human muscle fatigue, such as lactate, ammonia, and hydrogen ion, provide an incomplete and unsatisfactory explanation of the fatigue/recovery process, and it is likely that additional unknown agents participate (Baker, A. J., K. G. Koston, R. G. Miller, M. W. Weiner (1993) "Slow force recovery after long-duration exercise: metabolic and activation factors in muscle fatigue" *J. Appl. Physiol.* 74:2294–2300;Bazzarre, T. L., S. D. Murdoch, S. L. Uw, D. G. Herr, I. P. Snider (1992) "Plasma amino acid responses of trained athletes to two successive exhaustive trials with and without interim carbohydrate feeding" *J. Am. Coll. Nutr.* 11:505–511; Dohm, G., G. J. Kasperek, E. B. Tapscott, H. A. Barkakat (1985) "Protein metabolism during endurance exercise" *Fed. Proc.* 44:348–352; Edwards, R. H. T. (1983) "Biochemical basis of fatigue in exercise performance. Catastrophy theory of muscle fatigue" In: *Biochemistry of Exercise, Proceedings of the Fifth International Symposium on the Biochemistry of Exercise* (H. G. Kutrgen, J. A. Vogel, and J. Poormans, eds.); MacDougall, J. D., M. A. Tarnopolsky, A. Chesley, S. A. Atkinson (1992) "Changes in muscle protein synthesis following heavy resistance exercise in humans: a pilot study" *Acta Physiol. Scand.* 146:403–404; and Walser, M., N. D. LaFrance, L. Ward, M. A. Van Duyn (1987) "Progression of chronic renal failure in patients given ketoacids following amino acids. *Kidney Int.* 32:123–128).

α-ketoisocaproate (α-KIC) is the ketoacid parent chain of L-leucine (i.e., it is L-leucine without the amino nitrogen), and is the first metabolite in the muscle catabolic pathway of leucine following reversible transamination to glutamate. The intermediary metabolism of α-KIC and leucine plays a major role in regulatory muscle biochemistry, integrity, and physiology (Abrumrad, N. N., Wise, K. L., Williams, P. E. (1982) "Disposal of α-ketoisocaproate: roles of liver, gut and kidneys" *Am. J. Physiol.* 243:E123–E131; Buse, M. G. and S. S. Reid (1975) "Leucine: a possible regulator of protein turnover in muscle" *J. Clin. Invest.* 56:1250–1261; Flakoll, P. J., M. J. VanderHaar, G. Kuhlman, S. Nissen (1991) "Influence of α-ketoisocaproate on lamb broth, feed conversion, and carcass composition" *J. Anim. Sci.* 69:1461–1467; Harper, A. E., R. H. Miller, K. P. Block (1984) "Branched-chain amino acid metabolism" *Ann. Rev. Nutr.* 4:409–454; Jeevanandam, M., M. R. Ali, N. J. Holaday, J. K. Weis, R. Peterson (1993) "Relative nutritional efficacy of arginine and ornithine salts of α-ketoisocaproic acid in traumatized rats" *Am. J. Clin. Nutr.* 57:889–896; and Tarnopolsky, M. A., S. A. Atkinson, J. D. MacDougall, B. B. Senor, P. W. R. Lemon, H. Schwartz (1991) "Whole body leucine metabolism during and after resistance exercises in fed humans" *Med. Sci. Sports Exerc.* 23:324–333).

In some instances erosion of muscle mass induced by overtraining or injury can be reduced by metabolic intervention (Blomstrand, E. and E. A. Newsholme (1992) "Effect of branched-chain amino acid supplementation of the exercise-induced change in aromatic amino acid concentration in human muscle" *Acta Physiol. Scand.* 46:293–298; and Mori, E., M. Hasebe, K. Kobayashi, H. Suzuki (1989) "Intermediate stimulation of protein metabolism in burned rats by total parenteral nutrition enriched in branched-chain amino acids" *J. Panenter. Enteral. Nutr.* 13:(5):484–489) with metabolites of leucine, although in humans leucine itself elevates serum and intramuscular ammonia as it is utilized as a local fuel (MacLean, D. A. and T. E. Grahm (1993) "Branched-chain amino acid supplementation augments plasma ammonia responses during exercise in humans" *J. Appl. Physiol.* 74:2711–2717 and MacLean, D. A., T. E. Grahm, B. Saltin (1994) "Branched-chain amino acids augment ammonia metabolism while attenuating protein breakdown during exercise" *Am. J. Physiol.* 267:E1010–E1022). Ammonia ($NH_3$) arises from the deamination of adenosine monophosphate to inosine monophosphate in the purine nucleotide cycle, as well as from the deamination of branched-chain amino acids. The ability of tissues to re-aminate leucine from supplemental α-ketoisocaproate has been clinically exploited as a means to treat muscle wasting in acutely traumatized and critically ill patients, while reducing their nitrogen load (Harper, A. E., R. H. Miller, K. P. Block (1984) "Branched-chain amino acid metabolism" *Ann. Rev. Nutr.* 4:409–454. Traumatized, critically ill hospital patients with eroding muscle mass and nitrogen wasting have been aided with adjuvant dietary intervention using analogs of branched-chain ketoacids and dibasic acids (Mitch, W. E. M. Walser, D. G. Sapir (1981) "Nitrogen sparing induced by leucine compared with that induced by its keto analogue, α-ketoisocaproate, in fasting obese men" *J. Clin. Invest.* 67:553–562; Sapir, D. G., M. Walser, E. D. Moyer (1983) "Effects of α-ketoisocaproate and of leucine on nitrogen metabolism in postoperative patients" *Lancet* 1:1010–1014; and Warren, B. J., M. H. Stone, J. T. Kearney, S. J. Fleck, R. L. Johnson, G. D. Wilson, W. J. Kraemer (1992) "Performance measures, blood lactate and plasma ammonia as indicators of overwork in elite junior weight lifters" *Int. J. Sports Med.* 13:372–376). Hospital and in vitro studies with medical patients exhibiting liver disease and attendant central portal encephalopathy, or renal disease, show that certain administered combinations of ketoacid/amino acid complexes improve muscle trauma recovery time, reduce serum ammonia, enhance injury repair, and yield long-term catabolic/anti-anabolic effects on muscle protein. Acute changes in biceps brachii or quadriceps femoris muscle inter-conversion of KIC and leucine occurs following heavy resistance training (MacDougall et al. (1992) "Changes in muscle protein synthesis following heavy resistance exercise in humans: a pilot study" *Acta Physiol. Scand.* 146:403–404).

Enhancing muscle recovery following trauma occurs not simply by administering oral or intravenous leucine alone, but instead it responds to increasing the steady-state concentration of α-ketoisocaproic acid. This anabolic ketoacid is a major factor in reducing protein catabolism, stimulating muscle synthesis, and sparing glucose oxidation, while stimulating insulin release. Indeed, α-ketoisocaproic acid is superior to leucine in this regard in human and rat muscle studies (Buckspan, R., B. Hoxworth, E. Cersosimo, J. Devlin, E. Horton, N. Abrumrad (1986) "Alpha-ketoisocaproate is superior to leucine in sparing glucose utilization in humans" *Am. J. Physiol.* 251:E648–E653).

The observed biochemical and physiological effects of oral leucine/α-KIC on muscle recovery involve several enzymes (Aftring, R. P., K. P. Block, M. G. Buse (1986) "Leucine and isoleucine activate skeletal muscle branched-chain a keto acid dehydrogenase in vivo" *Am. J Physiol.* 250:E599–E604; Buse, M. G. and S. S. Reid (1975) "Leucine: a possible regulator of protein turnover in muscle" *J. Clin. Invest.* 56:1250–1261; and Kasperek, G. J. (1989) "Regulation of branched-chain 2-oxo acid dehydrogenase activity during exercise" *Am. J. Physiol.* 256:E186–E190.): The most critical enzymes are BCAA-aminotransferase, the BCKA dehydrogeneases family, L-leucine dehydrogenase, and 3-methyl-2-oxobutanoate dehydrogenase. Enzyme concentrations of BCAA-aminotransferase are relatively unregulated at fairly steady-state levels in muscle. Therefore, transamination is reversibly catalyzed by BCAA-aminotransferase activity through mass action of available concentrations of α-ketoisocaproate, L-leucine, L-glutamate, α-ketoglutarate, and their ancillary metabolites. In the presence of the excessive $NH_3$ liberated from the purine nucleotide cycle activated during exercise or from glutamate dehydrogenase, L-leucine dehydrogenase provides a beneficial pathway that catalyzes the $NH_3$ amination of α-ketoisocaproate to yield L-leucine. The enzyme 3-methyl-2-oxobutanoate dehydrogenase can catalyze the decarboxylation of α-ketoisocaproate, leading to pathways eventually creating acetoacetate. Alpha-ketoisocaproic acid can be hydrolyzed to beta-hydroxy-betamethylbutyrate via α-ketoisocaproate dioxygenase. (Harper, A. E., R. H. Miller, K. P. Block (1984) "Branched-chain amino acid metabolism" *Ann. Rev. Nutr.* 4:409–454; VanKoevering, M., S. Nissen (1992) "Oxidation of leucine and alpha-ketoisocaproate to beta-hydroxy beta-methylbutyrate in vivo" *Am. J. Physiol.* 262(1 pt 1):E27–31). It has been suggested that beta-hydroxybeta-methybutyrate may be involved in partially preventing muscle degradation and promoting muscle gain in chronic resistance training (Nissen, S. et al. (1996) "Effect of leucine metabolite beta-hydroxy-beta-methylbutyrate on muscle metabolism during resistance-exercise training" *J. Appl. Physiol.* 81:2095–2104). In contrast to unregulated BCAA-aminotransferase, the activity of BCKA-dehydrogenase is highly regulated during exercise. In muscle and liver, BCKA-dehydrogenase is a multienzyme complex that catalyzes the irreversible oxidative decarboxylation of BCKA, as it reduces NAD to NADH. The activity of BCKA-dehydrogenase greatly increases immediately after strenuous exercise, with subsequent return to resting baseline levels by 10 minutes post-exercise (Kasperek, G. J. (1989) "Regulation of branched-chain 2-oxo acid dehydrogenase activity during exercise" *Am. J. Physiol.* 256:E186–E190). BCKA-dehydrogenase enzyme activity is regulated by an ATP phosphorylation (inactivation)-dephosphorylation (activation) mechanism. α-ketoisocaproate is a key stimulator of this enzyme complex, whereby it inhibits the ATP-mediated kinase allosteric inactivation of BCKA-dehydrogenase. The potency of α-ketoisocaproate is several orders of magnitude greater than any other BCKA BCKA-dehydrogenase activity is therefore mediated by exercise and nutritional factors at the levels of allosteric and substrate mass action.

Control of muscle dysfunction with intravenous or dietary amino acids administered in the purified "free" form, especially branched-chain amino acids (BCAA), has been attempted in many studies (Grunewald, K.K. and R. S. Bailey (1993) "Commercially marketed supplements for bodybuilding athletes" *Sports Med.* 15:90–103; and MacLean, D. A., T. E. Grahm, B. Saltin (1994) "Branched-chain amino acids augment ammonia metabolism while attenuating protein breakdown during exercise" *Am. J Physiol.* 267:E1010–E1022). There are no substantiated guidelines for orally supplemented branched-chain amino acids because there have been no reputable double-blind controlled studies conducted to establish their effects; the use of BCAA in athletes is largely anecdotal and without systematic testing of performance. In contrast, however, it has been clearly established that intramuscular protein catabolism is decreased, protein synthesis is increased, and serum ammonia is decreased by metabolic intervention with branched-chain α-ketoacid (BCKA) analogs of BCAA, and that their effect may be enhanced by simultaneous administration of amino acids (Pui, Y. M. L. and H. Fisher (1979) "Factorial supplementation with arginine and glycine on nitrogen retention and body weight gain in the traumatized rat" *J Nutr.* 109:240–246; and Smith, K. and M. J. Rennie (1990) "Protein turnover and amino acid metabolism in human skeletal muscle. In: *Baillier's Clinical Endocrinology and Metabolism* 4:461–498).

L-Arginine is considered a "conditionally essential" amino acid that becomes essential under certain metabolic conditions including muscle trauma and injury (Dundrick, P. S. and W. W. Souba (1991) "Amino acids in surgical nutrition" *Surg. Clin. N. Am.* 71:459–476 and Smith, K. and M. J. Rennie (1990) "Protein turnover and amino acid metabolism in human skeletal muscle. In: *Baillier's Clinical Endocrinology and Metabolism* 4:461–498). L-Arginine is a dibasic amino acid that participates in the urea cycle and other intermediary pathways, notably serving as the starting substrate for biosynthesis of polyamines. Polyamines are essential for protein synthesis, and cell growth and proliferation. Arginine synergetically promotes the nitrogen-retaining effects of α-KIC. Studies show that cationic analogs such as ornithine, citrulline, or lysine may not be as effective as arginine, and may indeed inhibit the cell membrane transporters serving arginine (Kilberg, M. S., B. R. Stevens, D. A. Novak (1993) "Recent advances in mammalian amino acid transport" *Annu. Rev. Nutr.* 13:137–165; Mitch, W. E., M. Walser, D. G. Sapir (1981) "Nitrogen sparing induced by leucine compared with that induced by its keto analogue, α-ketoisocaproate, in fasting obese men" *J Clin. Invest.* 67:553–562; Pan, M., B. R. Stevens, W. W. Souba (1994) "Regulation of intestinal amino acid transport:

A surgical perspective" *Contemp. Surg.* 44:213–220; Pan, M., M. Malandro, B. R. Stevens (1995) "Regulation of System y+ arginine transport capacity in differentiating human intestinal Caco-2 cells" *Am. J. Physiol.* 268:G578–G585; and Pan, M. and B. R. Stevens (1995) "Differentiation- and protein kinase C-dependent regulation of alanine transport via system B" *J. Biol. Chem.* 270:3582–3587).

Previous studies showed that ornithine, lysine, and histidine salts of α-ketoglutaric acid, beta-hydroxy-beta methylbutyric acid, α-keto-beta-methylvaleric acid, and other ketoacid analogs of branched-chain amino acids promote positive nitrogen balance (Nissen et al. (1996) "Effect of leucine metabolite beta-hydroxy-beta-methylbutyrate on muscle metabolism during resistance-exercise training" *J. Appl. Physiol.* 81:2095–2104; VanKoevering, M., S. Nissen (1992) supra; Cynober, L., C. Coudray-Lucas, J -P deBandt et al. (1990) "Action of ornithine α-ketoglutarate, ornithine hydrochloride, and calcium α-ketoglutarte on plasma amino acid and hormonal patterns in healthy subjects" *J. Am. Col. Nutr.* 9:2–12; Cynober, L., M. Vaubourdolle, A. Dore, J. Giboudequ (1984) "Kinetics and metabolic effects of orally administered ornithine α-ketoglutatarate in healthy subjects fed with a standard regimen" *Am. J. Clin.* 39:514–519; Funk, M. A., K. R. Lowry, D. H. Baker (1987) "Utilization of the L- and DL-stereoisomers of a α-keto-β-methylvaleric acid by rats and comparative efficacy of the keto analogs of ranched-chain amino acids provided as ornithine, lysine, and histidine salts" *J. Nutr.* 117:1550–1555; Sitren, H. S. and H. Fisher (1977) "Nitrogen retention in rats fed on diets enriched with arginine and glycine" *Br. J. Nutr.* 37:195–208; Visek, W. J. (1986) "Arginine needs, physiological state and unusual diets: A reevaluation" *J. Nutr.* 116:36–46; and Wolf, J. G. Staleness. *In Encyclopedia of Sports Sciences and Medicine,* L. A. Larson and D. E. Hermann (Eds) New York: MacMillan Publishing Co. (1971) pgs. 1048–1050). Leucine or other BCAA alone did not demonstrate this effect (Buckspan, R., B. Hoxworth, E. Cersosimo, J. Devlin, E. Horton, N. Abrumrad (1986) "Alpha-ketoisocaproate is superior to leucine in sparing glucose utilization in humans" *Am. J. Physiol.* 251:E648–E653; Cersosimo, E., B. M. Miller, W. Lacy, N. N. Abrumrad (1983) "Alpha-ketoisocaproate, not leucine, is responsible for nitrogen sparing during progressive fasting in normal male volunteers" *Surg. Forum* 43:96–98; Sandstedt, S., L. Jorfeldt, J. Larsson (1992) "Randomized, controlled study evaluating effects of branched chain amino acids and α-ketoisocaproate on protein metabolism after surgery" *Br. J. Surg.* 79:217–220). Therapeutic strategies for recovery of medical or longitudinal muscle trauma have recently demonstrated the synergistic importance of dibasic amino acid salt complexed with ketoacids. Traumatized, critically ill hospital patients with chronic eroding muscle mass and nitrogen wasting have been aided with adjuvant dietary intervention using analogs of branched-chain ketoacids and dibasic acids (Nitch, W. E., M. Walser, D. G. Sapir (1981) "Nitrogen sparing induced by leucine compared with that induced by its keto analogue, α-ketoisocaproate, in fasting obese men" *J. Clin. Invest.* 67:553–562; Sapir, D. G., M. Walser, E. D. Moyer et al. (1983) "Effects of α-ketoisocaproate and of leucine on nitrogen metabolism in postoperative patients" *Lancet* 7:1010–1014; Warren, B. J., M. H. Stone, J. T. Kearney, S. J. Fleck, R. L. Johnson, G. D. Wilson, W. J. Kraemer (1992) "Performance measures, blood lactate and plasma ammonia as indicators of overwork in elite junior weight lifters" *Int. J Sports Med.* 13:372–376).

BRIEF SUMMARY OF THE INVENTION

The subject invention concerns methods and compositions for enhancing muscle performance and recovery from fatigue. More specifically, the subject invention concerns a unique metabolic intervention to improve athletic dynamic muscle strength and muscle work, and recovery from acute exhaustive anaerobic strength training exercise.

In a preferred embodiment the subject invention concerns the use of a glycine and L-arginine monohydrochloride salt of alpha-ketoisocaproic acid calcium (GAKIC) via oral treatment to a human or animal to enhance muscle performance and recovery from fatigue.

GAKIC has the following advantages:

1) GAKIC treatment increases the ability to sustain athletic muscle force during intense anaerobic muscle exercise;

2) GAKIC treatment increases the ability to sustain athletic muscle work during intense anaerobic muscle exercise; and 3) GAKIC increases the overall muscle performance by decreasing muscle absolute fatigue while retarding the rate of muscle fatigue.

In accordance with the subject invention, oral metabolic intervention with GAKIC significantly improves athletic muscle performance compared to control isocaloric carbohydrate: (1) GAKIC treatment increases the ability to sustain muscle force (torque) up to at least 28% during intense acute anaerobic dynamic muscle exercise; (2) GAKIC treatment increases the ability to sustain muscle total work (joules) by up to 12% during the early phase of intense anaerobic dynamic muscle exercise; and (3) GAKIC increases the overall muscle performance by forestalling muscle fatigue during the early phases of anaerobic exercise.

The subject invention also concerns a new testing protocol which is able to objectively test, quantify and provide a reproducible assessment of muscle work, fatigue, and recovery of dynamic muscle function associated with acute anaerobic exercise. This protocol was exploited to discriminate the effects of metabolic interventions on muscle function during training regimes.

The compositions and methods of the subject invention can be used to treat humans and animals. In one embodiment the materials and methods are used to treat horses.

BRIEF DESCRIPTION OF THE DRAWINGS

FIG. 2 shows the testing protocol overview.

DETAILED DISCLOSURE OF THE INVENTION

Figure 1:
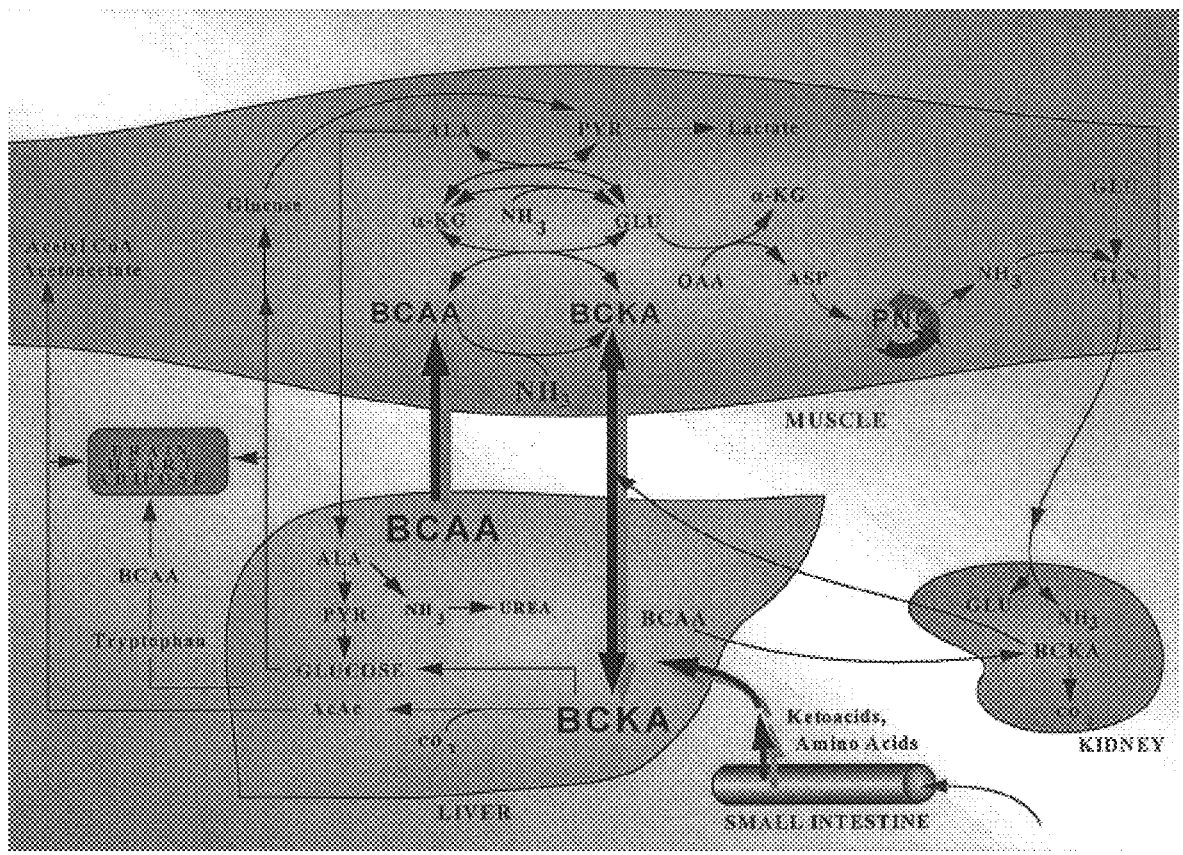
FIG. 1 shows a brief overview of the whole-body intermediary metabolic relationship among BCAA and BCKA.

The subject invention provides materials and methods that enhance muscle performance under conditions of acute exhaustive anaerobic dynamic exercise. The subject invention can be used to enhance human or animal muscle performance. Animals which can benefit from the subject invention include horses.

GAKIC, a novel formulation useful according to the subject invention, is safe for humans and animals. In a preferred embodiment, GAKIC comprises glycine, L-arginine, and α-ketoisocaproic acid. GAKIC can be used according to the subject invention as a nutritional supplement to enhance athletic performance. The benefits of GAKIC include at least the following:

1) A more rapid and complete recovery from intense acute athletic training, greater acute muscle power, and ultimately improved performance is achieved with GAKIC.

2) GAKIC is a safe means to enhance athletic performance, without the harmful side effects or illegality of anabolic steroids, pharmaceuticals or elevated caffeine.

3) In highly trained competing athletes, the significant muscle performance gain directly attributable to GAKIC can provide a winning edge among nearly equal competitors.

4) GAKIC can be useful to medical patients with sports injuries, as a means to improve exercise tolerance and recovery during rehabilitation.

5) The described exercise and testing protocol using the computerized isokinetic dynamometer is a unique and useful means to quantify/assess muscle force, work, and dynamic fatigue performance during concentric and eccentric contractions under well-controlled reproducible experimental conditions. These conditions are directly extrapolated to the real-world of athletic training and competition.

6) The described exercise and testing protocol using the computerized isokinetic dynamometer is a unique and useful means to quantify/assess muscle function in medical patients with sports injuries, as a means to improve exercise tolerance and recovery during rehabilitation.

7) The benefits of GAKIC can help improve animal jumping and racing performance.

In addition to, or instead of, L-arginine, the composition of the subject invention can comprises other cationic or dibasic amino acids. These amino acids may be, for example, ornithine, histidine, and/or lysine. In a further embodiment of the subject invention, glutamate and/or glutamine may be substituted for glycine. Also, other salts of alpha-ketoisocaproic acid may be used in the compositions of the subject invention. These salts may be, for example, the sodium or potassium salts. Alternatively, the free acid may be used. It should be noted that the subject invention is not limited only to the use of alpha-ketoisocaproic acid and its salts. Other related acids and salts may also be used. These other related acids and salts may be, for example, alpha-keto-isovaleric acid, alpha-keto-beta-methylvaleric acid, or pyruvic acid as the free acids or as a salt of calcium, potassium sodium, or as a conjugate.

The components of the compositions of the subject invention may be administered individually, as a mixture, or as covalent bonds, or other conjugate. For example, alpha-keto-isocaproic acid or alpha-keto-isovaleric acid, alpha-keto-beta-methylvaleric acid, or pyruvic acid can be conjugated with arginine. Thus, in a preferred embodiment, the subject invention pertains to the use of a ketoacid with a cationic amino acid to improve muscle performance and recovery from fatigue. Although L-isomers are preferred racemic mixtures may also be utilized.

One aspect of the subject invention pertains to a stable tripeptide comprised of glycine, L-arginine, and β-ketoisocaproate covalently linked by amide bonds. Advantageously, this orally consumed GAKIC precursor is readily hydrolyzed by human pancreatic proteases, yielding the appropriate components of GAKIC in vivo in the intestinal lumen or in vitro.

In one embodiment, a low calorie beverage is provided. In a specific embodiment, low calorie cranberry juice can be used.

In one embodiment, the components can be orally administered via capsules.

Oral administration of the subject glycine-arginine-α-ketoisocaproic acid formulation is preferred over the intravenous route, due to the coordinated metabolic communication (FIG. 1) between skeletal muscle, liver, kidneys and the splanchnic bed, notably the small intestine. Both the splanchnic and skeletal muscle regions are the body's major sites of branched-chain amino acid metabolism. Although oral administration is considered the best route, the intravenous route is available in subjects unable to receive oral administration.

Clinical studies show that human subjects can tolerate a 30 gm oral single bolus of single dibasic amino acids (e.g., L-arginine monohydrochloride), branched-chain amino acids, or 35 mmole/day of alpha-ketoacid (Barbul, A. (1985) "Arginne: Biochemistry, physiology, and therapeutic implications" *JPEN* 10:227–238 and Cerra, F. B. (1992) "Role of nutrition in the management of malnutrition and immune dysfunction of trauma" *J. Am. Coll. Nutr.* 11:512–518). Arginine has been administered intravenously at 30 g m per day for over a week with no adverse effects (Barbul, A. (1985) supra). Ketoacids have been given at over 10 gm per day for up to 10 months (Walser, M., N. D. LaFrance, L. Ward, M. A. Van Duyn (1987) "Progression of chronic renal failure in patients given ketoacids following amino acids. *Kidney Int.* 32:123–128). Safety guidelines (Cerra, F. B. (1992) supra) recommended nutrient loading to less than or equal to 1.5–2.0 gm amino acid per kg body weight per day, that is, 105 gm–140 gm per day for a typical 70 kg human. Doses beyond this amount may result in a possible benign side effect, namely gastrointestinal discomfort. The stated doses disclosed herein are much less than the stated upper limit safety range for a typical 70 kg subject (Benevenga, N. J. and R. D. Steele (1984) "Adverse effects of excessive consumption of amino acids" *Ann. Rev. Nutr.* 4:157–181 and Sandstedt, S., L. Jorfeldt, J. Larsson (1992) "Randomized, controlled study evaluating effects of branched chain amino acids and α-ketoisocaproate on protein metabolism after surgery" *Br. J. Surg.* 79:217–220), and are not given as a single bolus, but instead are distributed as fractional aliquots over a 45 to 75 minute period, and therefore are unlikely to cause gastrointestinal discomfort. In one embodiment the dosage may be as large as tolerated per the recommended safety guidelines.

The components of the compositions of the subject invention can be administered in an effective dosage which can be readily ascertained by a person skilled in the art having the benefit of the current disclosure. A person skilled in the art would appreciate that the ratios as well as the concentrations of components can be modified in order to achieve the desired effect of enhanced muscle performance and reduced muscle fatigue.

One aspect of the subject invention concerns unique protocols and assessment instruments which can be used to quantify the effects of metabolic intervention on muscle force, work, and fatigue associated with acute anaerobic exercise. These measurements standardize the results from each individual subject, thereby permitting meaningful comparisons within the repeated-measures randomized crossover design. In the literature, isokinetic fatigue is commonly assessed by measuring the number of repetitions a subject can perform before force levels drop below a certain standard percentage of peak torque, comparison of complete exhaustion relative to a maximal static force, or assessment of time to exhaustion (Lewis, S. F., C. S. Fuko (1998) "A new approach to studying muscle fatigue and factors affecting performance during dynamic exercise in humans" *Exercise Sports Med Rev.* 26:91–116). In one aspect, the current invention provides a novel Fatigue Resistance Index (FRI) which provides a uniform measure of dynamic fatigue resistance with respect to each subject's individual force output. The FRI provides a meaningful measure of the dynamic resistance to fatigue by allowing all subjects to perform the same concentric and eccentric fatigue protocol of four 35-repetition high intensity sets of 90°/sec knee extensions, regardless of fatigue rate. The protocol and assessment are in contrast to other methods which have attempted using isokinetic measurements to quantify exercise fatigue or by using bicycle ergometers, free weight trials, vertical leap tests, and treadmill running; these methods are not as sensitive to acute dynamic changes in muscle force.

Pre-fatigue and post-fatigue peak torque and total work values were measured in isolated quadriceps femoris of subjects using a computer-controlled isokinetic dynamometer over a 23 day interval. During testing, fasted subjects were given oral GAKIC or isocaloric carbohydrate over a 45 min period preceding exercise. Subjects then immediately performed four 35-repetition high intensity sets of 90°/sec knee extensions on the isokinetic dynamometer employing concentric and eccentric contractions. Measurements were made before and during the fatigue protocol. The effects of the treatments were tested in a randomized double-blind crossover repeated measures design (N=13 subjects). Additional parameters were maintained constant throughout the protocol: systolic and diastolic blood pressure, body weight, legg mass, and dietary L-leucine, L-arginine, glycine, total protein, total calories, total carbohydrate and caffeine. A novel Fatigue Resistance Index (FRI=[peri-exhaustion torque]/[baseline peak torque]) and a total work (TW) assessment (total work produced for the duration of each 35-repetition set) were each obtained during the muscle's concentric and eccentric phases for each set. This provided changes in fatigue over time. The mean baseline concentric isokinetic knee extension maximal torque was 240±9 Nm. The FRI and TW for each of the 35-repetition sets obtained at 0, 5, and 15 min following oral GAKIC was greater than for isocaloric carbohydrate (control). At these times, GAKIC treatment increased the mean FRI by 28%, 21%, and 13% above isocaloric carbohydrate values, respectively, while the TW per set was increased by GAKIC by 12%, 9%, and 11% respectively, above isocaloric carbohydrate values (overall mean percent gain in muscle TW attributable to GAKIC was 10.5±0.8% retained for at least 15 min.). After 24 hr, both GAKIC and placebo concentric forces returned to the same absolute values with mean FRI=0.41±0.05 (98 N·m/240 N·m), and mean TW=4600±280 joules. Analysis of values by order of treatment in the repeated measures crossover design (i.e., GAKIC or carbohydrate given in either first or second set of trials) indicated that there were no significant differences (P>0.05) attributable to the random order of testing. Compared to isocaloric carbohydrate, GAKIC treatment increased the muscle force and work generated during acute anaerobic exercise, while retarding the rate of fatigue, as assessed using the stated protocol.

The subject invention is also useful in extended, continual aerobic phases of intense exercise exceeding 15 min, but less than 24 hr of continuous exercise, that include both anaerobic glycolytic as well as oxidative metabolism due to the metabolic pathways employing the components of GAKIC. Thus, GAKIC can also be used for longitudinal weight-training.

MATERIALS AND METHODS

Basic design. The effects of GAKIC were studied using a repeated measures, randomized, crossover scheme conducted in a double-blind fashion, with subjects receiving both oral GAKIC (treatment) and oral isocaloric carbohydrate (sucrose placebo control) solutions, and with treatment measurements assessed against a non-treatment baseline established for each subject. Significant differences and trends were assessed by repeated measures ANOVA and/or paired t-tests. Data were recorded in real-time using Kin-Com 125 AP isokinetic dynamometer software (Chattanooga Group, Inc., Chattanooga, Tenn.).

Human subjects were recruited evenly between males and females from among all races and ethnic groups. The final pool of subjects (N=13) were all healthy male athletes involved in resistance training for a minimum of 6 months preceding the study. Subjects were free from the following metabolic conditions: diabetes-mellitus, aminoaciurias including maple syrup urine disease (congenital defect in branched-cahin ketoacid dehydrogenase), renal failure, muscle wasting, hypertension, abdominal radiotherapy or intestinal resection, fever, steroid or immunosuppressant use. During the testing period subjects were monitored for dietary intake of L-leucine, L-arginine, glycine, total protein, total calories, total carbohydrate and caffeine. No significant differences (p>0.05) were found between the GAKIC and carbohydrate treatment periods for any dietary variable. Blood pressure, leg weight, and body weights were also monitored and determined to be constant (P>0.05) during the testing period; subjects were randomly assigned to each group, and were remunerated after completion of the entire series of visits.

Subject physical characteristics were measured during the randomly assigned carbohydrate and GAKIC treatment periods. Because the crossover design used the exact same subjects for both treatments, subject age (21±2) and height (72±2 inches) were the same. The carbohydrate and GAKIC treatment periods were not significantly different (p>0.05) with respect to body weight (82.93 vs. 82.74 lbs), limb weight (84.77 vs 86.15 Newtons), or in blood pressure immediately preceding to testing (117/74 vs. 119/73 mm Hg; systolic/diastolic).

Treatments. Each 11.20 gm of glycine-L-arginine-α-ketoisocaproicacid ("GAKIC") treatment formulation comprised 2.0 gm (17.85 wt %) of glycine, 6.0 gm (53.57 wt %) of L-arginine monohydrochloride, and 3.2 gm (28.57 wt %) of α-ketoisocaproic acid dicalcium. Subjects were given a solution to drink containing 11.20 gm freshly dissolved powdered GAKIC or 9.46 gm sucrose isocaloric placebo in 355 ml Publix®Reduced calorie Cranberry Juice (62% less calories than regular cranberry juice). This effectively provided the same taste in control and treatment solutions, as determined by hedonic assessment. Solutions were consumed in 3 aliquots over 45 minutes.

Protocol. Each subject was required to make five visits to the testing facility, with three visits in the fasted state. Force measurements and total work measurements were recorded with a Kin-Com 125AP isokinetic dynamometer. This computerized device permitted continual assessment of each subject's ability to produce dynamic muscular force and work over time. Peak torque, average torque, and work were analyzed from a full set of repetitions throughout every degree in the range of motion. An overall concept diagram of the protocol is shown in FIG. 2.

The Fatigue Resistance Index. The Fatigue Resistance Index (FRI) describes the maximal exerted force sustained under fatiguing conditions as a percent of maximal force exerted under fresh conditions for each individual over a period of time. FRI is based on the ability to produce concentric or eccentric torque immediately following maximal exertion over 30 initial repetitions of a 35 repetition set in the presence of metabolic treatment, compared to that same individual's ability to produce force under fresh (baseline) conditions in the absence of treatment. The fixed value of 35 maximal isokinetic concentric/eccentric repetitions to induce fatigue in the quadriceps muscle groups was determined based on a pilot study. A pilot study was initially employed to determine isokinetic fatigue conditions and muscle performance quantifications. Based on this pilot, fatigue was induced in the quadriceps muscle group during a fixed value of 35 maximal isokinetic concentric/eccentric repetitions. One week preceding initial fatigue testing, a Baseline Isokinetic Knee Extension Maximal Strength Value ("BIKEMSV", in peak torque units of Nm) was obtained at a rate of 90°/sec both concentrically and eccentrically. During subsequent fatigue test bouts associated with the metabolic treatments, the subjects then performed another sequence of 35 continuous isokinetic concentric/eccentric knee extension repetitions. Peak forces for both the concentric and eccentric phases obtained during the last 5 repetitions of each 35 rep set (i.e., peri-exhaustion torque) were analyzed. An average of these five peak values was calculated for both the concentric and eccentric phase of the muscular event. The FRI was calculated by dividing this average value by the maximal force generated during the BIKEMSV testing. Concentric and eccentric BIKEMSV values were determined for each subject during "Visit 1," described below. FRI was obtained for each set in the protocol (0', 5', 15', and 24 hr).

Total Work. Total work (TW) values for each 35 repetition set were also collected and derived from the Kin-Con 125AP software, and are expressed in units of joules produced during each set.

Isokinetic Dynamometer Instrumentation. Each subject's right knee was carefully aligned with the rotation axis of the dynamometer lever arm, and subjects were secured in place using a waist strap, two should straps, and a thigh stabilizer. The distal shin pad was adjusted for each subject and placed two finger breadths above the lateral malleolus. The shin pad was securely fastened to the level arm using a Velcro strap. Gravity compensation procedures were carried out according to manufactures recommendations with the knee in and extended position. Knee extension and flexion motion occurred in a 75° arc, so that start and stop angles were 85° and 10°, respectively.

Differences in the values of FRI and TW between the GAKIC trials and the isocaloric carbohydrate control trials were measured using repeated measures ANOVA or paired t-tests. Also assessed was the effect of treatment order. An a priori alpha significance level of 0.05 was used for all comparisons.

A Fatigue Resistance Index (FRI=[peri-exhaustion torque]/[baseline peak torque]) and a total work (TW) assessment (total work produced for the duration of each 35-repetition set) was obtained during the muscle's concentric and eccentric phases for each set. This provided changes in fatigue over time. The FRI and TW for each of the 35-repetition sets obtained at 0, 5, and 15 min following oral GAKIC was greater (P<0.02) than for sucrose (control). At these times, GAKIC treatment increased the mean FRI by 28%, 21%, and 13% above carbohydrate values, while the TW per set was increased by GAKIC by 12%, 9%, and 11% above carbohydrate values. After 24 hr, both GAKIC and carbohydrate concentric forces returned to the same absolute values (P>0.05) with mean FRI=41±5% (98 N·m/240 N-m), and mean TW=4600±280 joules. Analysis of values by order of treatment in the repeated measures cross-over design (i.e., GAKIC or carbohydrate given in either first or second set of trials) indicated that there were no significant differences (P>0.05) attributable to the random order of testing.

Statistical Considerations

Basic Design. This study is a repeated measures, randomized, crossover design conducted in a double-blind fashion, with subjects receiving both oral GAKIC (treatment) and oral sucrose (control placebo) solutions, and with treatment measurements assessed against a non-treatment baseline established for each subject. Significant differences and trends are assessed by repeated measures ANOVA and/or paired t-test using SigmaStat™ analysis software.

Randomization of "double-blind" procedure. Subjects were randomly assigned to each group by computer-generated randomization. An independent research associate kept records confidential and "blind" from the investigators until after data were analyzed.

Sample size. The number of subjects recruited conservatively exceeds the calculated sample size requirement from Power Analysis using the following conditions. These parameters were derived from preliminary experiments using a leg extension force apparatus and protocol: the detectable percent difference in means between two groups is better than a Force Resistance Index=5, with a population standard deviation of ±5. With the power set at 0.80 and with $\alpha$=0.05, then N=10 for a repeated measures paired t-test. The actual final sample size giving the present data was N=13.

The Experimental Model: Testing effects. When implementing a testing protocol on a naive subject, especially one utilizing an uncommon movement type like isokinetic exercise, there is always concern that the results might be affected by a testing or learning effect. This is an improvement in performance that may occur as a result of experience and coordination gained through multiple trials. The double-blind, repeated measures crossover design of this study was invoked to negate such possible testing effects. This design gave each group equal chance to be affected, therefore canceling out any impact of significance; there were no significant (p>0.05) differences in any treatment attributable to the random order of treatment (GAKIC or carbohydrate). In addition, the blinded testers administered a two set warm up teaching/practice phase to subjects each testing day preceding fatigue trials. Subjects performed 3 consecutive submaximal isokinetic right knee extensions at 90° /sec, followed by a maximal set of 3 repetitions. Snow and Blacklin (Snow, C. J., K. Blacklin (1992) "Reliability of knee flexor peak torque measurements from a standarized test protocol on a Kin/Com dynamometer" Arch. Phys. Med. Rehabil. 73:15–21) found much higher test-retest correlations when including within-session maximal contractions in warm-up procedures, as compared to between session practice. Thus, these small bouts served more as a coordination warm up than a physical one. These techniques were successful in protecting against a testing effect. When grouped by chronological order rather than according to treatment, there were no between-group differences for FRI nor TW (P>0.05).

The Experimental Model: Time variable. The speed at which the GAKIC supplement is absorbed and distributed to the skeletal muscle is not completely known, but typical rates of gastric emptying and intestinal absorption insure GAKIC was assimilated during the 60 on board over the 60 minute period of administration and testing (from −45 minutes through the end of the "15 min" exercise set). For this reason, subjects were administered three equal doses over a 45 minute preceding fatigue testing. This was to maximize the chances of having high muscle levels of GAKIC during the training bouts. Evidence of supplemental effect during the "0 minute" set narrows the effect time variable to between 30 seconds and 46 minutes.

Following are examples which illustrate procedures for practicing the invention. These examples should not be construed as limiting. All percentages are by weight and all solvent mixture proportions are by volume unless otherwise noted.

EXAMPLE 1

Testing Procedures

Visit 1

During the initial visit, subjects complete a medical history questionnaire and are screened by project personnel to ensure concurrence with the inclusion/exclusion criteria.

A maximal force-repetition baseline is initially obtained three times for each subject to measure changes in maximal force production and to quantify fatigue over time in ensuing experiments. Subsequent fatigue testing utilizes this value for both control and GAKIC treatments. The same-subject random crossover design of this project eliminates any minor biases that pretesting could potentially introduce.

Subjects are positioned on the Kin-Com 125AP isokinetic dynamometer. Once positioned, subjects are asked to produce submaximal efforts of quadriceps force production by right knee extension at 90°/sec during both the concentric and eccentric phases, with each phase again separated by a 15 second rest period. Following this warm-up exercise, subjects are asked to produce maximal efforts of right knee extension at 90°/sec during both the concentric and eccentric phases, with each phase again separated by a 15 second rest period. Subjects are given verbal encouragement throughout each maximal effort. Efforts continue until the same maximum peak torque curve has been achieved 3 times for each of the concentric as well as eccentric phase of muscle function.

Subjects are asked to return in one week for the second test visit. For this session, subjects are instructed to refrain from exercise of the lower extremity during the entire three week testing period. Subjects are asked to take a dietary record 24 hours preceding visit 2, and to fast for a period of 12 hours preceding subsequent visits.

Visit 2

Subjects have been instructed to fast (no food or beverages other than ad libitum water for 12 hours) prior to the exercise session. At the beginning of this visit, subjects complete a 24 hour history, and dietary recall. After being seated for 15 minutes, resting heart rate and blood pressure are measured. Subjects first engage in a practice/warm-up session. Subjects are restrained with a lap belt and two shoulder harnesses and are asked to perform all repetitions with arms crossed over the chest. The practice session is comprised of 3 consecutive concentric and eccentric repetitions, followed by a second set of 3 maximal concentric and eccentric repetitions. This practice session precedes delivery of GAKIC or placebo, to allow subjects to regain homeostasis prior to maximal testing.

Upon arrival of the subject, a research assistant randomly assigns and mixes either 11.20 gm GAKIC (glycine-arginine-α-ketoisocaproic acid) or 9.46 gm sucrose isocaloric placebo (pre-dispensed and coded by manufacturer) in 355 ml Publix® low calorie Cranberry juice. This is a double-blind study, and thus the examiners are unaware of which supplement is being administered, only the research assistant records this information for use by the investigators following statistical analysis. The 11.20 gm of GAKIC or 9.46 gm sucrose placebo is administered in three equal 3.73 gm doses (GAKIC) or three equal 3.15 gm doses (sucrose) at −45 (minus 45) minutes, −20 (minus 20) minutes, and 0 minutes prior to Quadriceps Fatigue Testing on the Kin-Com 125AP isokinetic dynomometer. These doses are dispensed in 3×118.3 mL aliquots of the 355 mL solution. Blood pressure is monitored 20 minutes prior to testing. Once the final "zero minute" dose of GAKIC or placebo is administered, the following fatigue testing protocol is initiated:

1) Immediately following the final administration of GAKIC or placebo (t=0 min), subjects perform 35 consecutive right knee concentric and eccentric contractions using maximal effort at a speed of 90°/sec. The examiner gives verbal encouragement throughout each 35 repetition sequence.

2) Exactly 5 minutes following the final administration of GAKIC or placebo, subjects perform a second set of 35 consecutive right knee concentric and eccentric contractions using maximal effort at a speed of 90°/sec. The examiner gives a verbal encouragement throughout each 35 repetition sequence.

3) Exactly 15 minutes following the third and final administration of GAKIC or placebo, subjects perform a third set of 35 consecutive right knee concentric and eccentric contractions using maximal effort at a speed of 90°/sec. The examiner gives verbal encouragement throughout each 35 repetition sequence.

4) Following this protocol and ample recovery time, subjects are dismissed and asked to return for testing after a 24 hour rest period. Subjects are allowed to eat or drink ad libitum, but are asked to document a written dietary record of everything consumed for analysis of consumed L-leucine, L-arginine, glycine, total protein, caffeine, total calories, and total carbohydrate, as calculated using the Minnesota Nutrition Data software (version 2.91) developed by the Nutrition Coordination Center at the University of Minnesota.

Visit 3

Twenty four hours following the treatment, fatigue testing is performed as described for visit 2, but is performed without delivery of GAKIC or placebo. Following 5 minutes of rest, the subject performs a set of 35 concentric and eccentric knee extension repetitions at 90°/sec. Subjects document a written record of dietary intake for subsequent analysis of consumed L-leucine, L-arginine, glycine, total protein, caffeine, total calories, and total carbohydrate, as for Visit 2. Subjects are instructed to return in 14 days for visit 4.

Visit 4

After 14 days, the same subjects crossover and repeat the protocol in a manner identical to Visit 2, with the assistant assigning and mixing the treatment which subjects did not receive in visit 2 (either 11.20 gm GAKIC glycine-arginine- α-ketoisocaproic acid: calcium salt, or 9.46 gm sucrose placebo in 355 ml Publix® Cranberry Juice) following another 12 hour fast with dietary recall records. During Visit 4, subjects again are seated on the Kin-com 125AP isokinetic dynamometer and perform the same practice session described in "Visit 2." Following 5 minutes of rest, subjects perform the set of 35 concentric and eccentric knee extension repetitions at 90°/sec. Subjects document a written record of dietary intake for subsequent analysis of consumed L-leucine, L-arginine, glycine, total protein, caffeine, total calories, and total carbohydrate, as for Visit 2. Subjects are instructed to return in 14 days for Visit 5.

Visit 5

Visit 5 is identical to visit 3. Twenty-four hours following the treatment, fatigue testing is performed as described for Visit 2, but is performed without delivery of GAKIC or placebo. Following 5 minutes of rest, the subject performs a set of 35 concentric and eccentric knee extension repetitions at 90°/sec.

Data Collection/Analysis.

Figure 3:
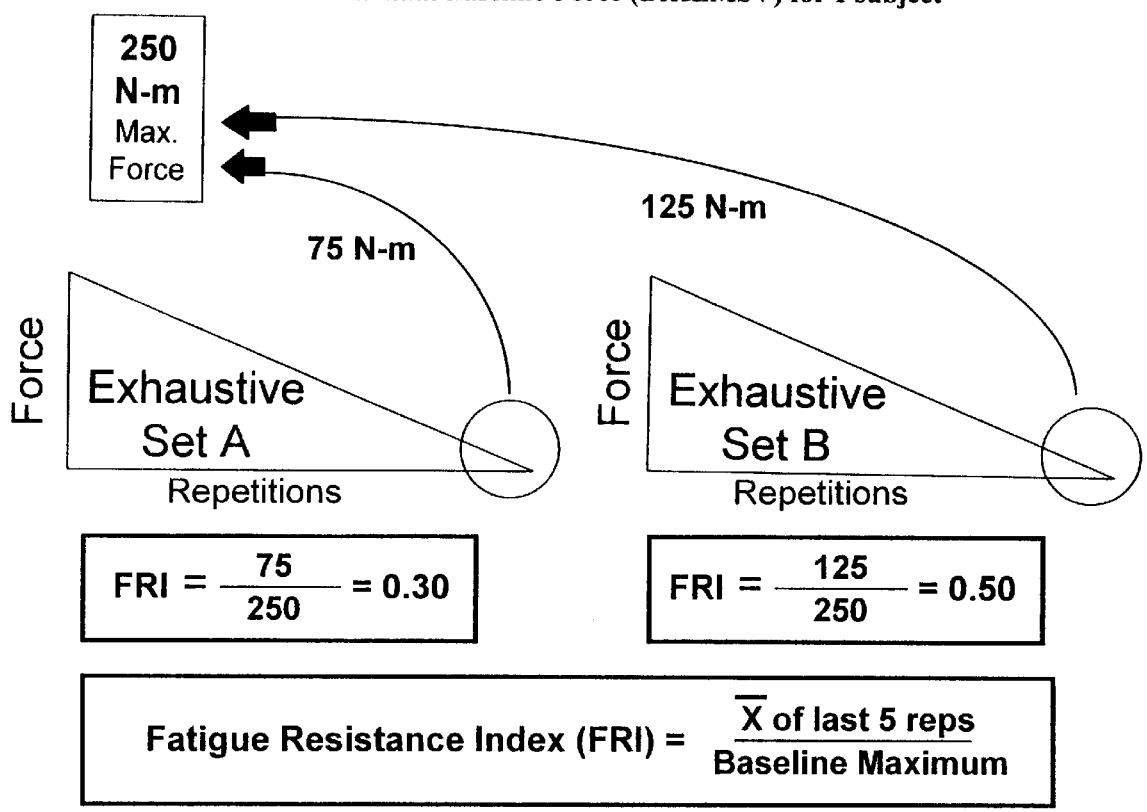
FIG. 3 shows a representative computation of the fatigue resistance index (FRI).

Measured torque is used as the dependent measure of force production. Torque produced during the last 5 repetitions of each 35 repetition testing set is used to calculate a mean torque value for the last five repetitions. The mean of these 5 repetitions is divided by the Baseline Maximal concentric or Baseline Maximal eccentric torque values determined during "Visit 1." This creates a "Fatigue Resistance Index" (FIG. 3) which represents the percentage of a subject's maximum ability to produce muscular force. Fatigue resistance reflects the subject's capability of sustaining dynamic muscular effort over a given time period. This ratio is obtained for each set in the protocol. A conceptual example comparing the "Fatigue Resistance Index" for two exercise sets is shown in FIG. 3 for a case of 250 Newton-meters maximal baseline force from a single subject. Similar calculations are obtained for each subject at each visit as outlined in the Testing protocol overview (see FIG. 2).

Total work for each set was measured. The values collected and derived from the Kin-com software are in units of joules produced during each set. Differences in the values of Fatigue Resistance ratio and total work between the GAKIC trials and the placebo trials are measured using repeated measures ANOVA or paired t-tests. The within-subjects group include treatment (GAKIC vs. placebo), and time following treatment oral administration(0, 5, 15 minutes, 24 hour). An a priori alpha significance level of 0.05 is used for all comparisons.

EXAMPLE 2

Concentric muscle fatigue resistance enhancement by GAKIC

Figure 4:
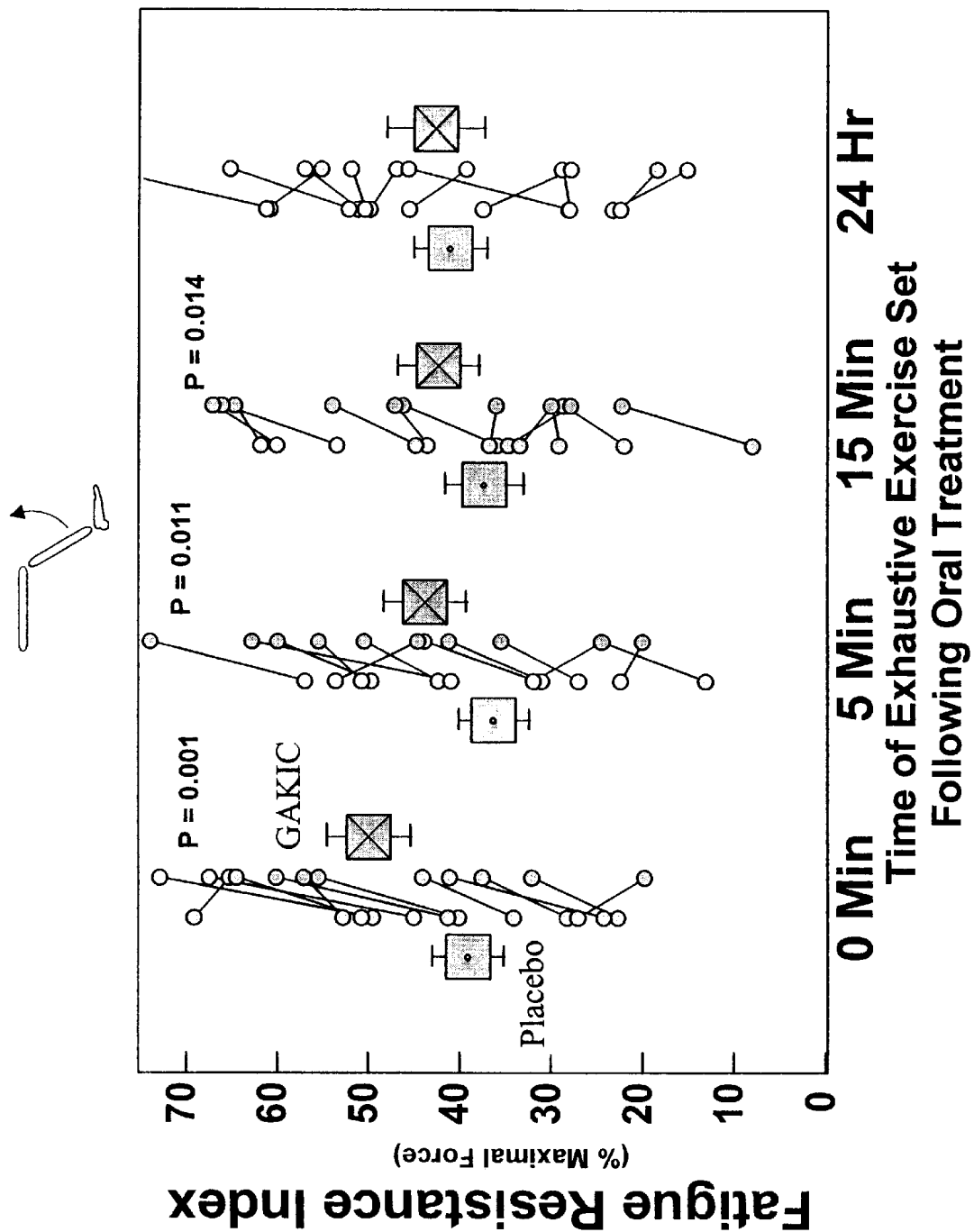
FIG. 4 shows the concentric muscle fatigue resistance enhancement by GAKIC.
Figure 5:
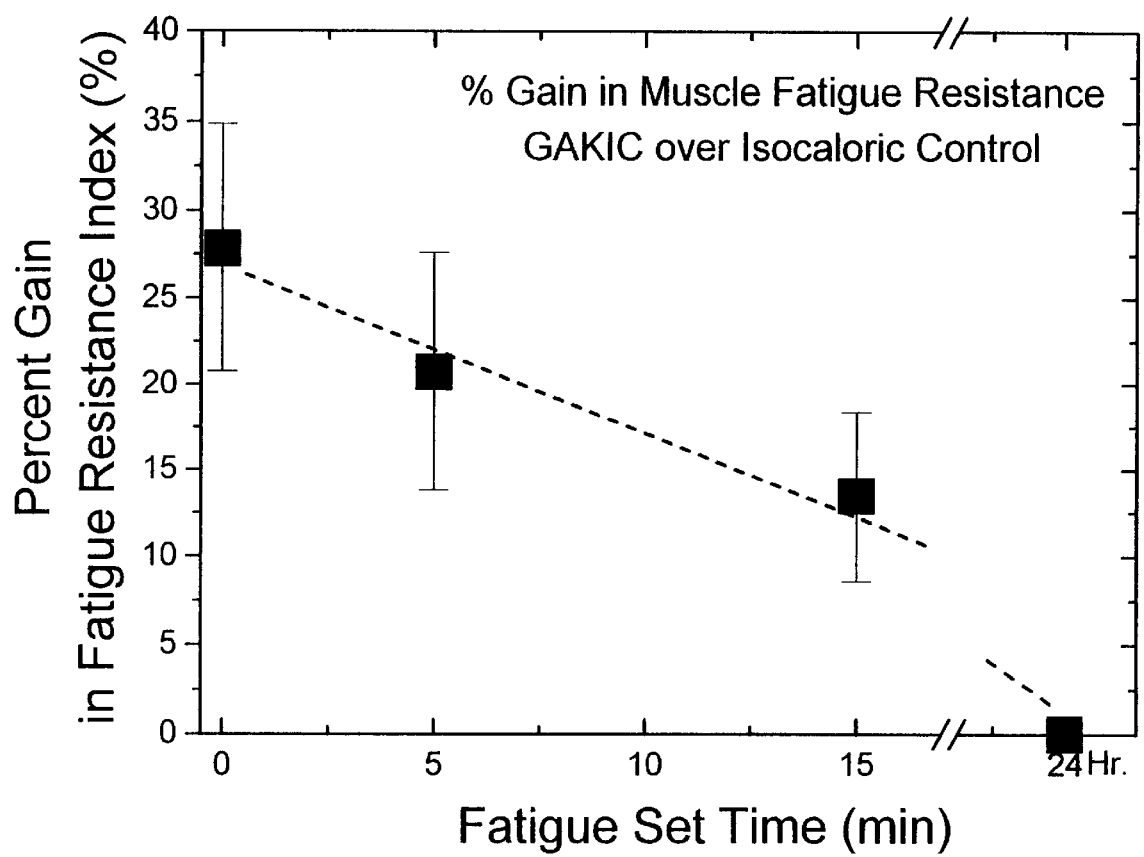
FIG. 5 shows the percent gain in fatigue resistance directly attributable to GAKIC treatment.

Fasted subjects (N=13; repeated measures crossover) consumed oral GAKIC or isocaric sucrose placebo, and then the concentric force excerted by their isolated right leg muscle (quadriceps femoris) was measured following an exhaustive exercise regime controlled by the Kin-com dynamometer. The concentric Fatigue Resistance Index (FRI), shown in FIG. 3, represented this force expressed as a percent of BIKEMSV. Greater FRI values indicated the ability of GAKIC treatment to sustain significantly greater muscle force (torque) and to significantly (p<0.02) reduce acute muscle fatigue. Mean significant differences were sustained at 0 min (50.2% vs. 39.2%), 5 min (44% vs. 36.4%), and 15 min (42.6% vs. 37.5%) for these same-subject repeated measures crossover paired comparisons, as shown in FIG. 4. After 24 hr recovery, the treatment groups were not significantly different (P>0.05). The mean baseline concentric isokinetic knee extension maximal torque was 241±9 Nm. The concentric FRI for each of the 35-repetition sets obtained at 0, 5, and 15 min following oral GAKIC treatment was greater (P<0.02) than for isocaloric carbohydrate (control). At these times, GAKIC treatment increased the mean FRI by 28%, 21%, and 13%, respectively, above isocaloric placebo control (carbohydrate) values. See FIG. 5. These data indicated that GAKIC treatment increased the ability to maintain a higher percentages of the subjects' concentric baseline isokinetic knee extension maximum strength value (BIKEMSV) over these periods. After a 24 hour washout period, both GAKIC and placebo concentric forces were restored to the same absolute values with mean FRI=0.41±0.05 (i.e., 98 N·/240 N·m).

Analysis of values by order of treatment in the repeated measures cross-over design (i.e., GAKIC or placebo in either first or second set of trials) indicated no significant differences (P>0.05) at any time point, thus validating the random nature of the treatment assignment order.

EXAMPLE 3

Total work performed during each fatigue set for the concentric phase

Figure 6:
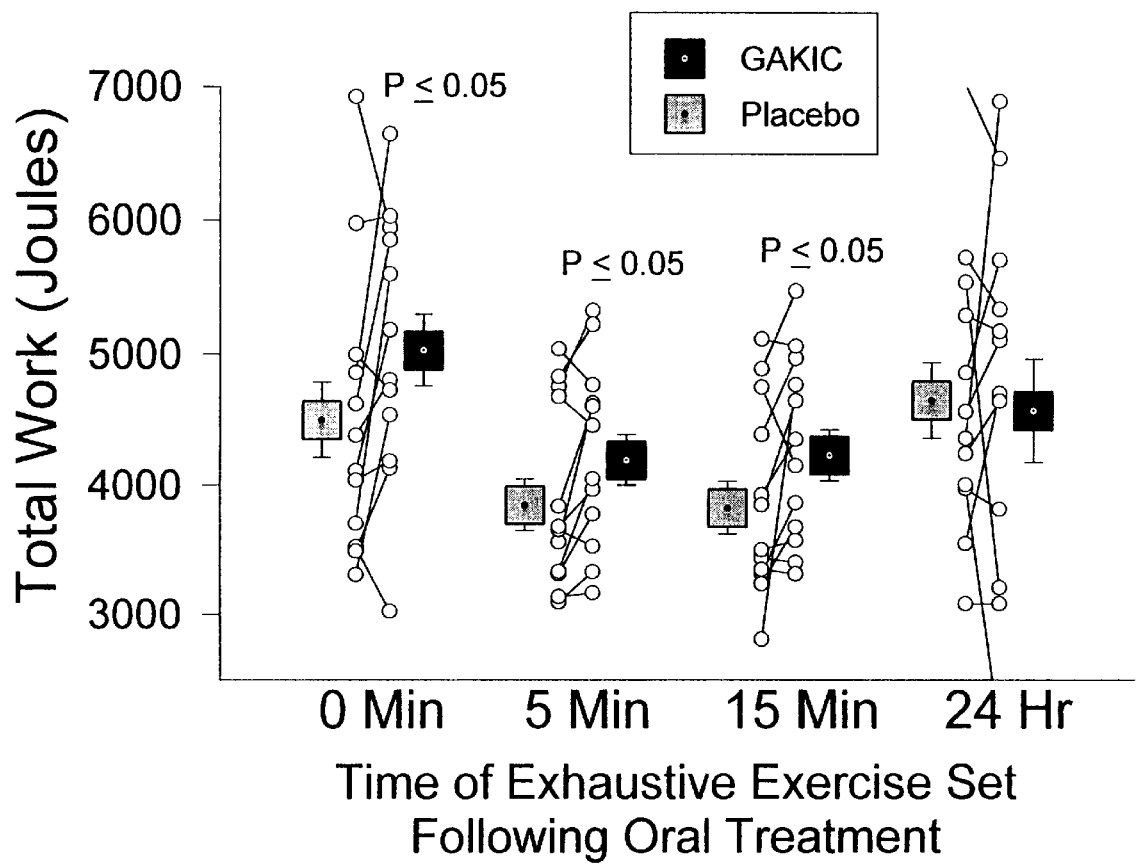
FIG. 6 shows the total work performed during each fatigue set for the concentric phase.

GAKIC treatment means (±SEM) are significantly greater than placebo means (P≦0.05) by repeated measures (N=13 subjects) comparisons for each 35-repetition set except after 24 hr recovery, when the treatment groups were not significantly different (P>0.05). See FIG. 6.

Figure 7:
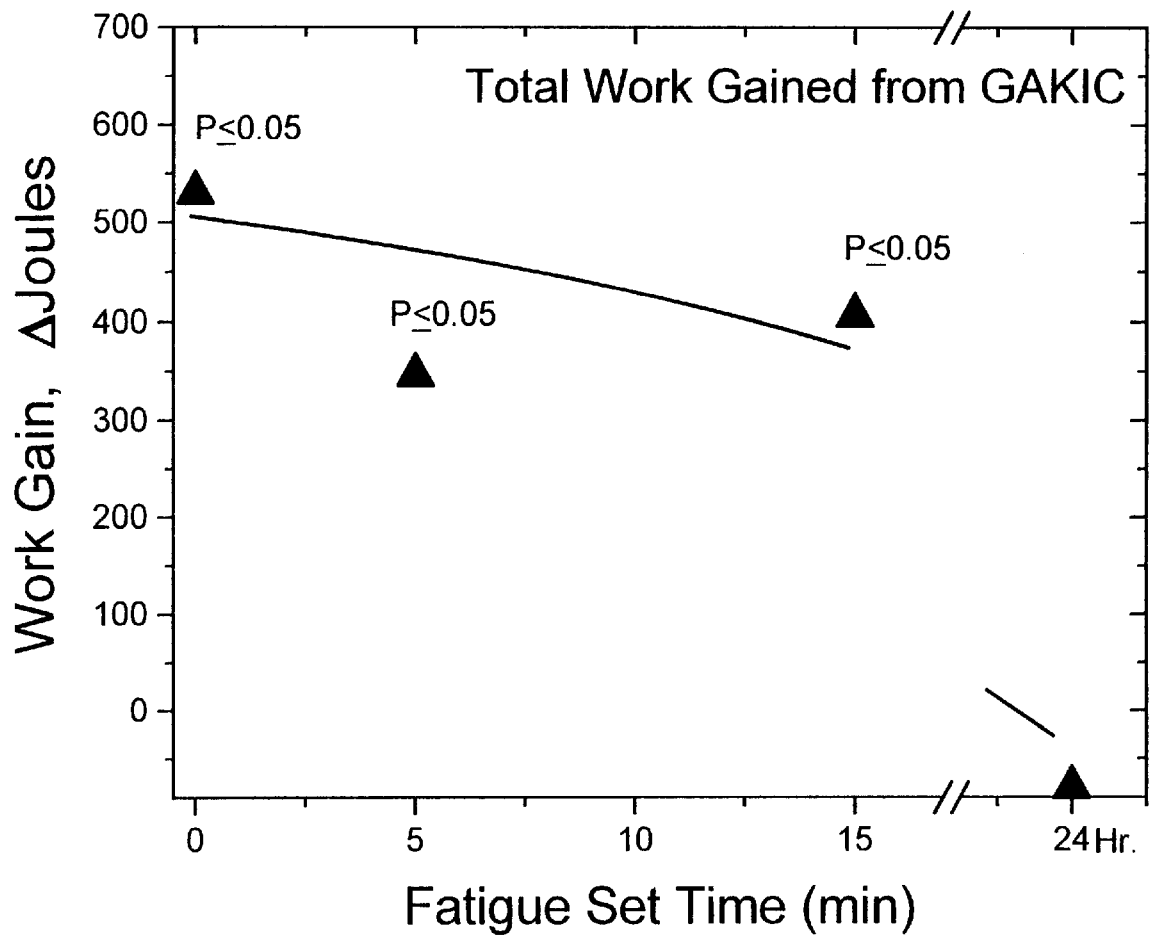
FIG. 7 shows the work gained from GAKIC treatment.

For each 35-repetition fatigue set the difference in total concentric muscle work (joules) was obtained for placebo and GAKIC treatments. This Δ joules value represents the gain in concentric work directly attributable to GAKIC. The indicated points are significantly different (P≦0.05) from (e.g., greater than) sucrose placebo group values treatment (N=13 repeated measures cross-over design). After 24 hour recovery, values were not significantly different (P>0.05). See FIG. 7.

Figure 8:
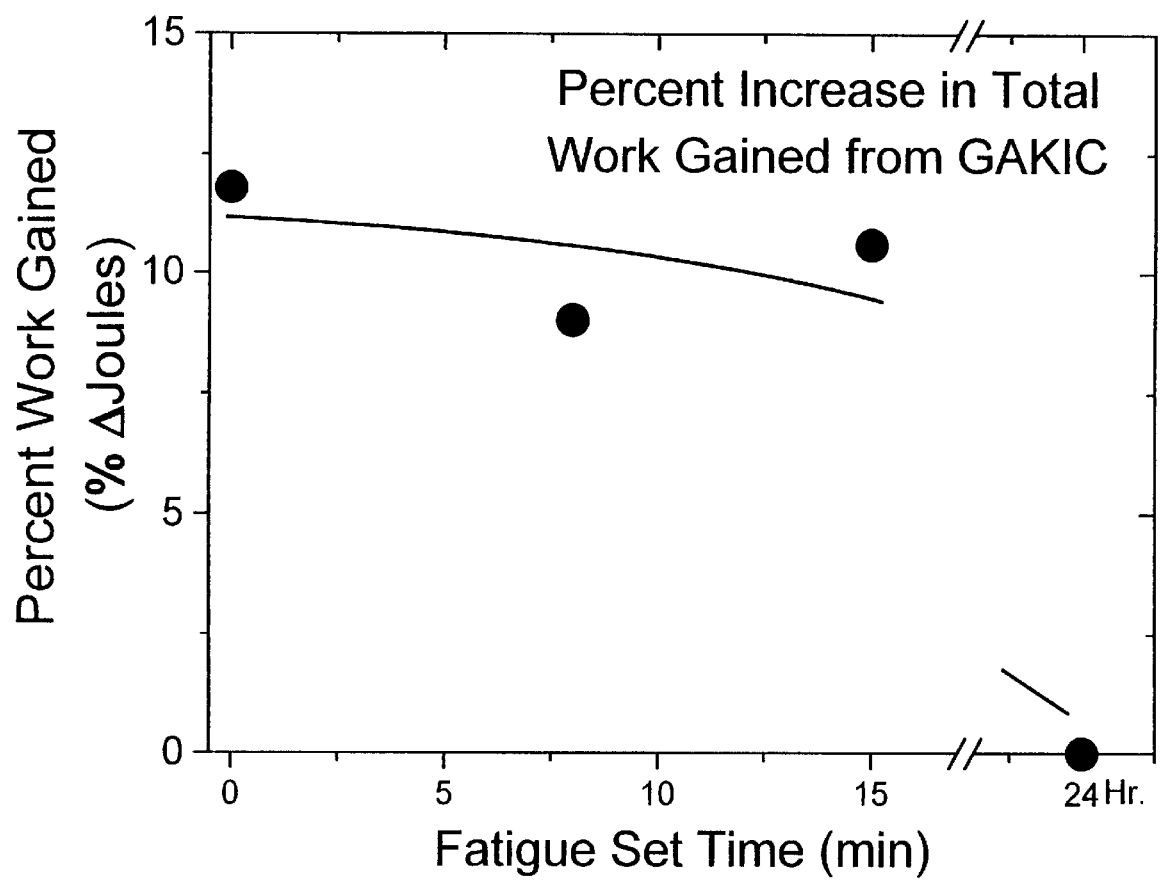
FIG. 8 shows the percent increase in total work gained from GAKIC treatment.

The TW value is a measure of a subject's ability to sustain total work output across time. TW values (joules) were obtained by integrating the work performed during every repetition in a given set for both the concentric and eccentric phases of contraction. TW values could be affected by changes in the absolute force peak level, changes in ability to sustain a given force peak level, or changes in magnitude of sustained force output during each repetition. During the 0, 5, and 15 min sets, GAKIC treatment resulted in greater concentric TW values compared to isocaloric carbohydrate treatment. At these times, GAKIC treatment increased the mean TW per set by 12%, 9%, and 11%, respectively, above isocaloric carbohydrate values. The overall mean percent gain in muscle total work attributable to GAKIC treatment was 10.5±0.8% retained for at least 15 min. See FIG. 8. The 24 hr washout period restored the effect of GAKIC treatment to the control mean value of TW=4600±280 joules.

It should be understood that the examples and embodiments described herein are for illustrative purposes and that various modifications or changes in light thereof will be suggested to persons skilled in the art are to be included within the spirit and purview of this application and the scope of the appended claims.

What is claimed is:

1. A method for enhancing muscle performance or recovery from fatigue wherein said method comprises administering a composition comprising a ketoacid and an amino acid wherein said amino acid is cationic or dibasic.

2. The method, according to claim 1, wherein said composition further comprises a compound selected from the group consisting of glutamate, glutamine, and glycine.

3. The method, according to claim 2, wherein said composition comprises glycine.

4. The method, according to claim 1, wherein said ketoacid is selected from the group consisting of α-ketoisocaproic acid, α-ketoisovaleric acid, α-ketobetamethylvaleric acid, pyruvic acid, and salts thereof.

5. The method, according to claim 4, wherein said composition comprises α-ketoisocaproic acid, or a salt thereof.

6. The method, according to claim 1, wherein said amino acid is selected from the group consisting of arginine, ornithine, histidine, and lysine.

7. The method, according to claim 6, wherein said composition comprises arginine.

8. The method, according to claim 1, wherein said amino acid and said ketoacid are conjugated.

9. The method, according to claim 1, wherein said composition is administered orally.

10. The method, according to claim 9, wherein said composition is administered as a low calorie beverage.

11. The method, according to claim 1, wherein said composition further comprises cranberry juice.

12. The method, according to claim 1, wherein said composition is administered orally by capsules.

13. The method, according to claim 1, wherein said composition is administered intravenously.

14. The method, according to claim 1, wherein said method results in an increase in the fatigue resistance index.

15. The method, according to claim 1, wherein said method increases the total work output.

16. The method, according to claim 1, wherein said method improves dynamic performance during concentric contraction.

17. The method, according to claim 1, wherein said method improves dynamic performance during eccentric contraction.

18. The method, according to claim 1, wherein said method is used on a human.

19. The method, according to claim 1, wherein said method is used on a horse.

* * * * *

UNITED STATES PATENT AND TRADEMARK OFFICE
CERTIFICATE OF CORRECTION

PATENT NO.   : 6,100,287
DATED        : August 8, 2000
INVENTOR(S)  : Bruce R. Stevens, et. al.

It is certified that error appears in the above-identified patent and that said Letters Patent is hereby corrected as shown below:

Column 3, line 27: "a keto" should read --α keto--.

Column 3, line 33: "BCAA" should read --BC$\underline{A}$A--.

Column 3, line 34: "BCKA" should read --BC$\underline{K}$A--.

Column 3, line 50: "-betamethylbutyrate" should read -- -beta-methylbutyrate--.

Column 8, line 1: "β-ketoisocaproate" should read --α-ketoisocaproate--.

Column 10, line 20: "125  AP" should read --125AP--.

Column 14, line 11: "administered, only" should read --administered; only--.

Signed and Sealed this

First Day of May, 2001

Attest:

NICHOLAS P. GODICI

*Attesting Officer*    *Acting Director of the United States Patent and Trademark Office*